United States Patent [19]
Torchilin et al.

[11] Patent Number: 5,567,410
[45] Date of Patent: Oct. 22, 1996

[54] COMPOSOTIONS AND METHODS FOR RADIOGRAPHIC IMAGING

[75] Inventors: Vladimir P. Torchilin, Charlestown; Vladimir S. Trubetskoy, Milton; Gerald L. Wolf, Winchester; G. Scott Gazelle, Hingham, all of Mass.

[73] Assignee: The General Hospital Corporation, Boston, Mass.

[21] Appl. No.: 265,421

[22] Filed: Jun. 24, 1994

[51] Int. Cl.$^6$ .......................... A61K 49/04; C07C 63/10; C07C 233/65; C07C 25/02
[52] U.S. Cl. ................ 424/9.4; 424/9.45; 514/5; 514/561; 514/563; 514/568; 514/617; 514/754; 530/402; 562/465; 562/474; 564/188; 570/182
[58] Field of Search ................ 424/9.45, 9.4; 514/561, 5, 563, 568, 617, 754; 530/402; 562/465, 474; 564/188; 570/182

[56] References Cited

U.S. PATENT DOCUMENTS

| | | | |
|---|---|---|---|
| 3,733,397 | 5/1973 | Bjork et al. | 424/5 |
| 4,192,859 | 3/1980 | Mackaness et al. | 424/9.45 |
| 4,728,575 | 3/1988 | Gamble et al. | 428/402.2 |
| 4,830,858 | 5/1989 | Payne et al. | 424/450 |
| 5,145,853 | 10/1992 | Newkome et al. | 252/311 |
| 5,233,995 | 8/1993 | Yudelson et al. | 128/662.02 |
| 5,238,714 | 8/1993 | Wallace et al. | 427/213.36 |
| 5,258,172 | 11/1993 | Rubin | 424/9.45 |
| 5,264,610 | 11/1993 | Bacon | 424/9.45 |
| 5,308,614 | 5/1994 | Sinn et al. | 424/1.53 |
| 5,354,549 | 10/1994 | Klaveness et al. | 424/9.45 |

FOREIGN PATENT DOCUMENTS

| | | |
|---|---|---|
| 0397307 | 11/1990 | European Pat. Off. . |
| 0436316A1 | 7/1991 | European Pat. Off. . |
| 0498482A2 | 8/1992 | European Pat. Off. . |
| 0583955A2 | 2/1994 | European Pat. Off. . |
| 1400985 | 7/1975 | United Kingdom . |
| 2240547 | 8/1991 | United Kingdom . |

OTHER PUBLICATIONS

Adzami et al., "Production and Characterization of Improved Liposomes Containing Radiographic Contrast Media", *Investigative Radiology*, 25:1217–1223 (1990).

Kataoka et al., "Block copolymer micelles as vehicles for drug delivery", *Journal of Controlled Release*, 24:119–132 (1993).

Mattrey, "Blood–Pool Contrast Media Are the Ideal Agents for Computed Tomography", *Investigative Radiology*, 26:S55–S56 (1991).

Pratten et al., "Micelle–forming block copolymers: Pinocytosis by macrophages and interaction with model membranes", *Makromol. Chem.*, 186:725–733 (1985).

Revel et al., "Iodinated Polymer as Blood–Pool Contrast Agent, Computed Tomography Evaluation in Rabbits", *Investigative Radiology*, 26:S57–S59 (1991).

Yokoyama et al., "Characterization and Anticancer Activity of the Micelle–forming Polymeric Anticancer Drug Adriamycin–conjugated Poly(ethylene glycol)–Poly(aspartic acid) . . . ", *Cancer Res.*, 50:1693–1700 (1990).

Yokoyama et al., "Preparation of Adriamycin–conjugated poly(ethylene glycol)–poly(aspartic acid) block copolymer", *Makromol. Chem., Rapid Commun.*, 8:431–435 (1987).

Yokoyama et al., "Toxicity and Antitumor Activity against Solid Tumors of Micelle–forming Polymeric Anticancer Drug and Its Extremely Long Circulation in Blood", *Cancer Research*, 51:3229–3236 (1991).

*Primary Examiner*—Gary E. Hollinden
*Attorney, Agent, or Firm*—Fish & Richardson P.C.

[57] ABSTRACT

A radiographic imaging agent including a plurality of block copolymers forming a micelle, the block copolymers including a hydrophilic polymer linked to a hydrophobic polymer, and the hydrophobic polymer including a backbone incorporating radiopaque molecules via covalent bonds.

20 Claims, 8 Drawing Sheets

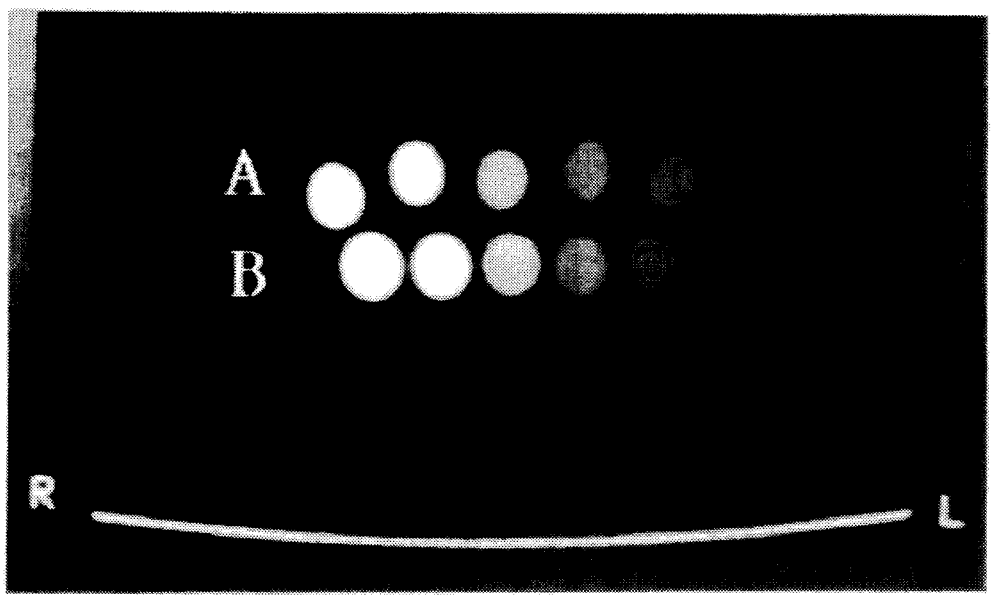
FIG. 6
FIG. 9A  FIG. 9B
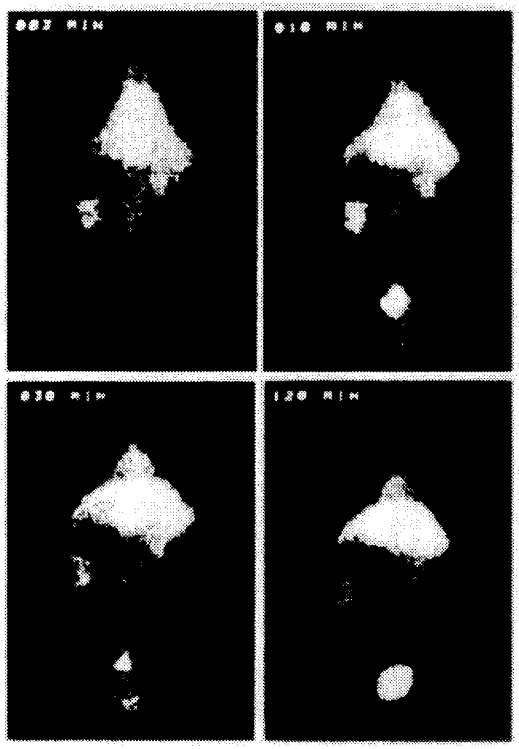
FIG. 9C  FIG. 9D
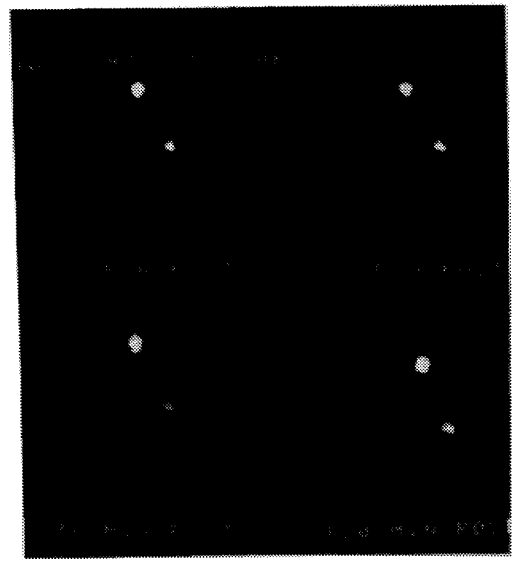
FIG. 13

COMPOSOTIONS AND METHODS FOR RADIOGRAPHIC IMAGING

BACKGROUND OF THE INVENTION

The present invention relates to contrast agents for radiographic imaging.

Radiographic imaging is widely used for the detection and diagnosis of various disease states. Methods such as plain film radiography, fluoroscopy, and digital radiography are two-dimensional imaging techniques which involve the projection of X-rays through individuals in order to produce visual images. Different tissues, based on their electron density, attenuate X-rays to different degrees. Radiation which is projected through the individual is detected and used to create an image which reflects the electron density of tissues lying between the X-ray source and detector. Computed tomography is a cross-sectional imaging technique which utilizes a rotating X-ray beam source to pass X-rays through an individual at different angles, and can thereby produce images with excellent spatial resolution in three dimensions. Unfortunately, intrinsic tissue contrast with CT is limited. This is due primarily to the fact that many tissues are composed of elements of similar electron density.

To improve the ability to detect normal structures, and to identify abnormalities involving those structures, contrast enhancement using exogenously administered contrast agents is considered essential. Contrast agents currently available are radiopaque, low molecular weight, water soluble, organic molecules, such as salts of iodine-containing aromatic molecules (e.g., diatrizoate and metrizoate). These radiopaque contrast agents result in greater attenuation of X-rays than most normal tissues in the human body, and therefore can lead to increased tissue contrast. The agents are usually injected intravenously into patients. However, due to their small size, they exhibit only a transient intravascular phase before diffusing into the interstitial space, where they provide little useful tissue contrast. In order to effectively utilize these contrast agents, administration and imaging must be performed rapidly so that images are acquired prior to diffusion into the interstitial space.

One approach to develop agents that remain in the intravascular space for prolonged periods of time (blood pool agents) is to create molecules that are significantly larger than the currently used agents, and that cannot readily diffuse from the blood vessels to the interstitial space. Unfortunately, such agents have proved difficult to develop. One approach has been to utilize molecules such as diatrizoate or metrizoate adsorbed onto particles. See, e.g., European Patent No. 498,482. Higher molecular weight contrast agents formed by radical polymerization of iodine-containing aromatic molecules have also been described. See, e.g., Lopour, et al., *Proc. of 34th IUPAC Int. Symposium on Macromolecules,* 3-P18 (1992). However, these higher molecular weight contrast agents are often too large to be excreted via the kidney, and thus are not easily eliminated from the body.

Micelle-forming block copolymers containing hydrophilic and hydrophobic portions have been used for in vivo delivery of anti-cancer pharmaceuticals (reviewed in Kataoka, et al., *J. Controlled Release,* 24:119–132, 1993). These micelle-forming copolymers have the ability to dissociate into their constituent polymer chains, or unimers, upon appropriate dilution, which allows their excretion. Additionally, certain hydrophilic polymers are adapted for allowing blood circulation of linked residues for prolonged periods of time.

SUMMARY OF THE INVENTION

The present invention relates to novel radiographic imaging agents in the form of micelles in aqueous solutions. These micelles are made of individual block copolymers that include a hydrophilic polymer linked to a hydrophobic polymer. The hydrophobic polymer includes a polymeric backbone which incorporates radiopaque molecules via covalent bonds. As used herein, "linked" means covalently or noncovalently bonded.

In general, the invention features a compound capable of forming micelles in an aqueous solution, the compound including a hydrophilic polymer, e.g., an uncharged polymer with a terminal reactive group, linked to a hydrophobic polymer, the hydrophobic polymer including a backbone incorporating radiopaque molecules via covalent bonds.

The hydrophilic polymer can be polyethylene glycol, polyethylene oxide, polyvinylpyrrolidone, polyacrylamide, poly-(N-hydroxypropyl)-methacrylamide, polyvinylalcohol, a polymethacrylate, a polysaccharide, a polyamino acid, or a polyacrylic ester, or a derivative thereof.

As used herein, a "derivative" is a compound or molecule whose core structure is the same as, or closely resembles that of, a parent compound, but which has a chemical or physical modification, such as a different or additional side groups, which allows the derivative to be linked to another molecule.

The backbone can be an amino-containing polymer, a polymer of amino acids, e.g., poly-L-lysine, a polycarboxylic acid, a polyanhydride, a polyhydroxy acid, a polysaccharide, polystyrene, polyisoprene, polyalkalene oxide, or a derivative thereof.

The radiopaque molecule can include an element with a heavy nucleus, e.g., an iodine-containing molecule such as diatrizoate, iothalamate, metrizoate, iodipamide, or triiodobenzoic acid, or a bromine-containing molecule such as perfluorooctyl bromide (PFOB).

In preferred embodiments, the hydrophilic polymer has a molecular weight of 10,000 to 15,000 daltons, e.g., 12,000 daltons, the backbone has a molecular weight of 3000 to 6000 daltons, and the hydrophobic polymer has a molecular weight of 9,000 daltons, the hydrophilic polymer is polyethylene glycol, and the backbone is poly-L-lysine.

The invention also features a method of imaging a region in a patient, e.g., an animal or human, by administering a diagnostically effective amount of the compound of the invention in the form of micelles to the patient, exposing the region to radiation, and obtaining an image of the region by detecting the micelles of the compound. This method can be used to image, e.g., the blood pool, the liver or spleen, or the lymph nodes.

As used herein, a "diagnostically effective amount" of the imaging agent is an amount that can be detected within a targeted region in a patient and thereby improve tissue contrast.

The invention further features a radiographic imaging agent including a plurality of block copolymers forming a micelle, the block copolymers including a hydrophilic polymer linked to a hydrophobic polymer, and the hydrophobic polymer including a backbone incorporating radiopaque molecules via covalent bonds.

The invention also features a targeted radiographic imaging agent including a plurality of block copolymers forming a micelle and a targeting ligand, e.g., an antibody, sugar molecule, enzyme, or hormone, linked to the block copolymers, the block copolymers including a hydrophilic polymer linked to a hydrophobic polymer, and the hydrophobic polymer including a backbone incorporating radiopaque molecules via covalent bonds.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

DESCRIPTION OF THE DRAWINGS

FIG. 6 is a CT scan of various dilutions of TIBPL(9)-PEG(12) and standard contrast agents.

FIGS. 9A to 9D are whole body scintigraphy scans of a rabbit at various times subsequent to intravenous injection with $^{111}$In-labelled TIBPL(9)-PEG(12).

FIG. 13 is a lymphoscintigraphy scan of a rabbit at various times subsequent to subcutaneous injection with $^{111}$In-labelled TIBPL(9)-PEG(12).

DETAILED DESCRIPTION

The present invention is a micellar iodine-containing block copolymer (MICBC) useful as a radiographic imaging agent. These micelle-forming block copolymers include a hydrophilic polymer linked to a hydrophobic polymer that includes a backbone incorporating radiopaque molecules. The imaging agent incorporates high levels of radiopaque molecules, which are normally insoluble, into the backbone of the hydrophobic polymer. The hydrophilic polymer imparts solubility to the imaging agent, and also allows it to avoid quick uptake by the reticuloendothelial system (RES). The micellar imaging agent thus allows high quantities of radiopaque molecules, adequate to permit detection with current imaging techniques, to be administered to an individual.

The micellar imaging agents are of sufficient size (approximately 100–150 nm) that they do not quickly diffuse into the interstitial space upon intravenous administration. Therefore, using MICBCs, radiographic imaging can be performed for longer periods of time than with low molecular weight contrast agents. MICBCs are especially useful for radiographic imaging of the blood pool; that is, the image of any vascularized region of the body can be enhanced by in vivo administration of MICBCs.

Additionally, despite the high molecular weight of the MICBCs when administered as micelles, MICBCs are excreted via the kidney after the micelles break down. After MICBCs are administered intravenously, they are diluted in the bloodstream, and the micelles ultimately dissociate into individual block copolymer chains, or unimers. These unimers are of low molecular weight, and are therefore efficiently eliminated from the body.

The rate at which MICBCs dissociate in vivo is a function of the molecular weights of the hydrophilic polymer and the backbone of the hydrophobic polymer, which together form the block copolymer. At the optimal molecular weights of each of these two polymer chains, the micellar structure exists for forty minutes to two hours once introduced into bodily fluids, during which time radiographic imaging can be performed. MICBCs then dissociate into low molecular weight unimers and are eliminated from the body.

MICBCs also can be modified to function as targeted diagnostic agents. Targeting ligands, such as antibodies directed to certain regions of the bodies, can be incorporated into the micelle in order to deliver high quantities of the imaging agent to a specific area.

Radiographic Imaging Agents

Radiographic imaging agents are micelles made of the block copolymers of the invention. These block copolymers include a hydrophilic polymer linked to a hydrophobic polymer, which includes a backbone incorporating radiopaque molecules.

Figure 1:
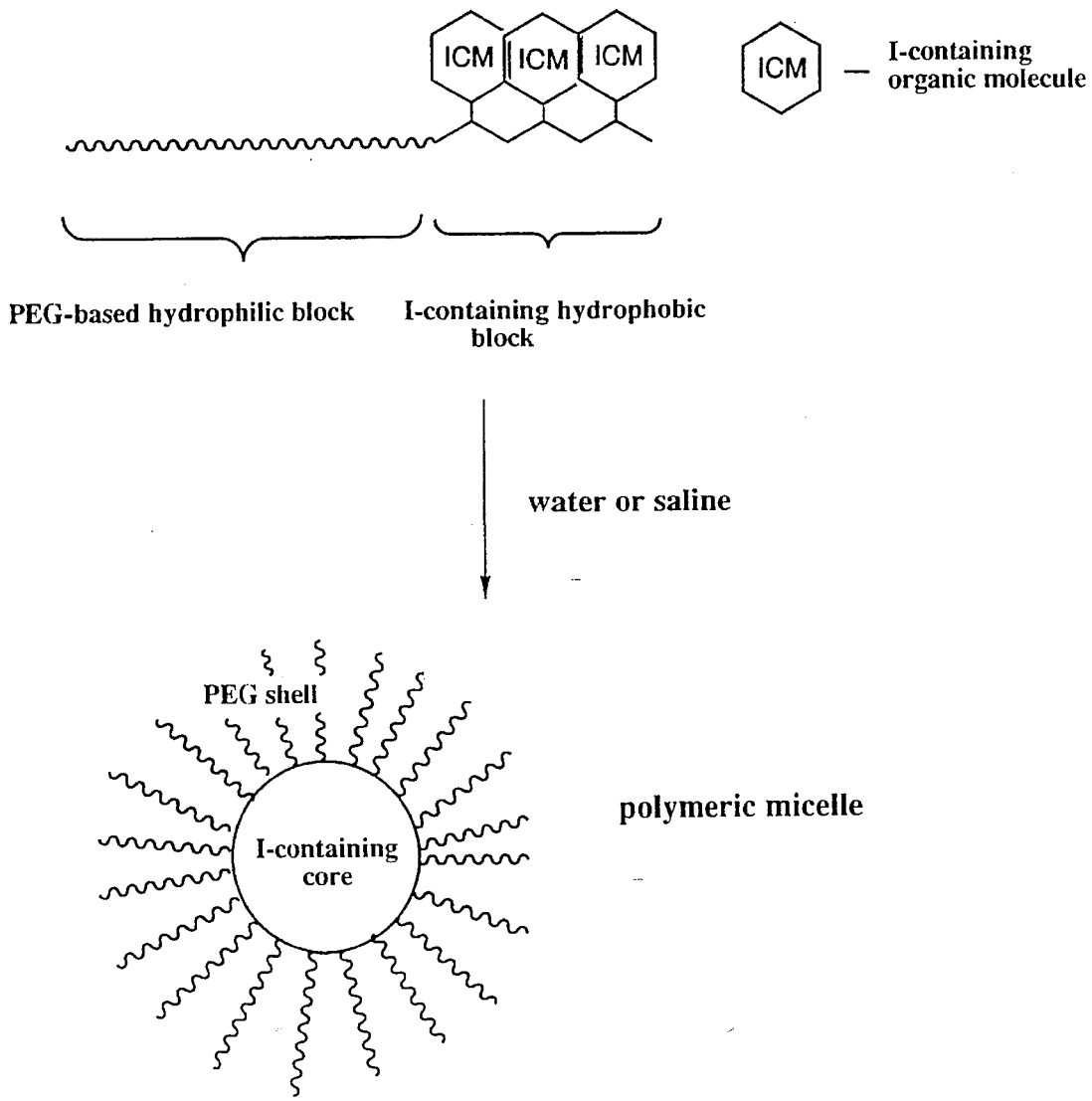
FIG. 1 is a schematic diagram showing a micelle formed of block copolymers containing radiopaque molecules.

Formation of a representative radiographic imaging agent is shown schematically in FIG. 1. A hydrophilic polymer (PEG-based hydrophilic block) is linked to a hydrophobic polymer (iodine-containing hydrophobic block). The hydrophobic polymer includes a backbone incorporating radiopaque molecules (iodine-containing organic molecules, or ICM) via covalent bonds. In aqueous solution, these block copolymers with radiopaque molecules form micelles composed of a hydrophilic outer shell (PEG shell), and a hydrophobic inner core (I-containing core).

Hydrophilic Polymers

The hydrophilic polymer of the block copolymer is preferably flexible and uncharged and includes a terminal reactive group. Preferred hydrophilic polymers include polyethyleneglycol (PEG), polyethylene oxide (PEO), polyvinylpyrrolidone (PVP), polyacrylamide (PA), poly-(N-hydroxypropyl)-methacrylamide, polyvinylalcohol (PVA), polysaccharides, polymethacrylates (PMA), polyacrylic esters, polyamino acids, and copolymers and derivatives thereof.

Hydrophobic Polymer

The hydrophobic polymer is a backbone and the attached radiopaque molecules. The backbone is preferably a polymer containing reactive side groups. Although the overall character of this "hydrophobic polymer" of the block copolymer is hydrophobic, the backbone itself can be a hydrophilic polymer, as long as incorporation of hydrophobic radiopaque molecules imparts an overall hydrophobicity to the combination of the backbone and the attached radiopaque molecules.

Preferred hydrophobic polymers include polyhydroxy acids such as polylactic acid or polymalic acid; polyanhydrides; polystyrene; polyisoprene; polyalkalene oxide; long chain alcohols; and derivatives thereof.

Preferred hydrophilic polymers include amino-containing polymers such as aminodextran polyethyleneimine, or any polyamine; polymers of amino acids such as poly-L-lysine, polyglutamic acid, or polyaspartic acid; polycarboxylic acids such as polyacrylic acid or polymethacrylic acid; polysaccharides; and derivatives thereof.

The radiopaque molecules are incorporated into the polymeric backbone at its reactive side groups via covalent bonds. The radiopaque molecules are preferably any molecules containing an element with a heavy nucleus such as iodine and bromine. Iodine-containing molecules must be able to react with the side groups of the polymeric backbone. These molecules include diatrizoate, iothalamate, metrizoate and iodipamide. A preferred iodine-containing molecule is triiodobenzoic acid. Also suitable are perfluorated bromine-containing molecules, such as perfluorooctyl bromide (PFOB).

Methods of Synthesis

In a preferred method of synthesis of the labeled block copolymers, (1) the terminal reactive group of a hydrophilic polymer is chemically activated, (2) the activated hydrophilic polymer is conjugated at its terminus to a polymeric backbone with protected side groups to form the block copolymer, (3) the polymeric backbone is subjected to deprotection of its side groups, and (4) radiopaque molecules are incorporated into the polymeric backbone at its reactive side groups. The resulting labeled block copolymers form the micellar iodine-containing block copolymer (MICBC) imaging agent.

Figure 2:
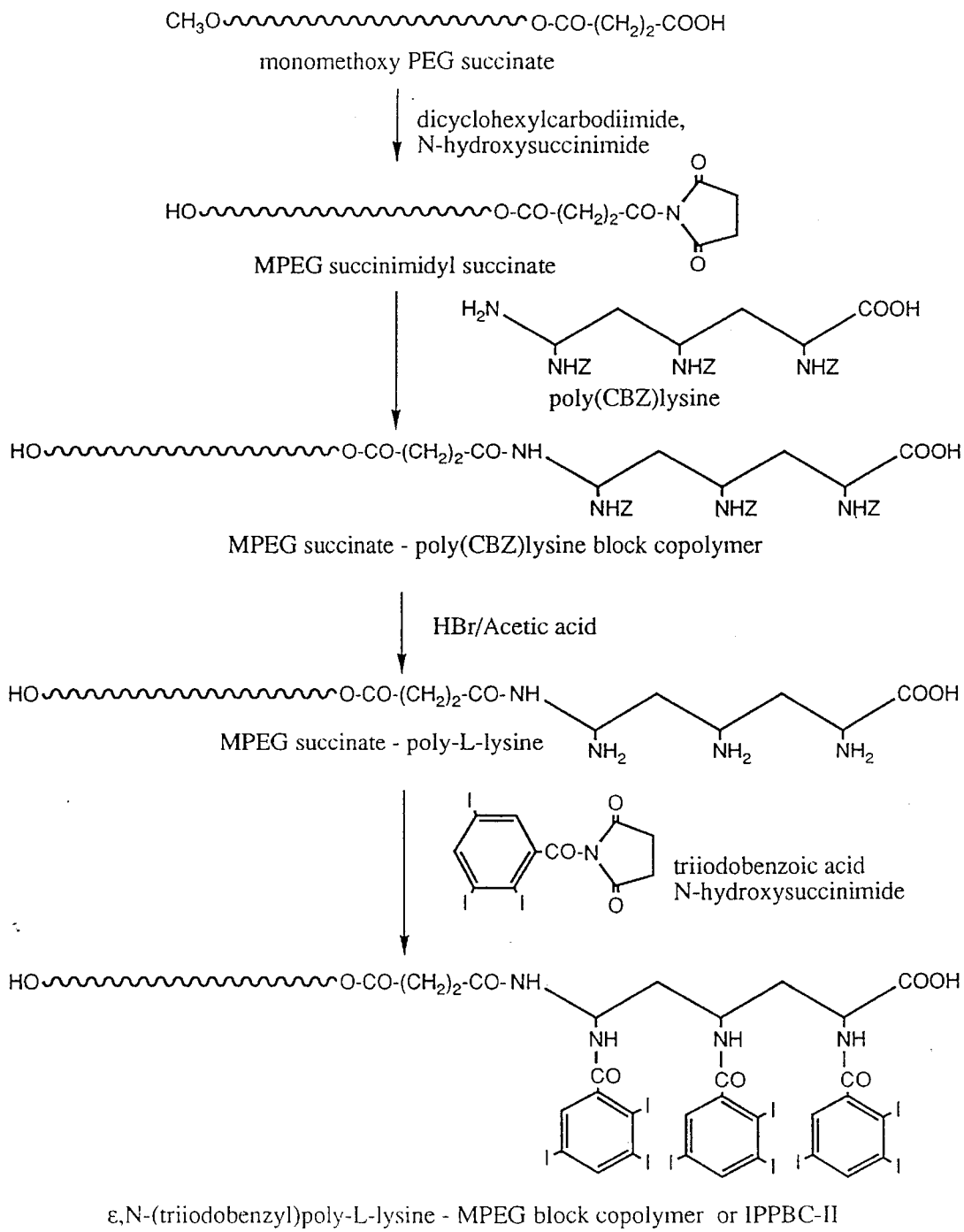
FIG. 2 is a schematic diagram showing the steps to synthesize N,α-[ε-(triiodobenzyl)poly-L-lysine] monomethoxypolyethylene glycol (TIBPL-PEG), a representative micellar iodine-containing block copolymer (MICBC).

FIG. 2 shows schematically the steps to synthesize N,α-[ε-(triiodobenzoyl) poly-L-lysine]monomethoxy-polyethylene glycol, a representative MICBC.

Synthesis of a Hydrophilic Polymer

A hydrophilic polymer, monomethoxypolyethylene glycol (MPEG) succinate (molecular weight 12,000 daltons (d)), was activated with dicyclohexylcarbodiimide (2.06 g, Sigma) and N-hydroxysuccinimide (1.15 g, Pierce) in 50 ml of dimethylformamide (DMFA). The reaction was allowed to proceed overnight at room temperature. The product, MPEG-succinimidyl succinate, was precipitated and washed three times with 50 ml dry diethyl ether.

Synthesis of a Block Copolymer

MPEG succinimidyl succinate (1.5 g) was mixed with a polymeric backbone, poly(carbobenzoxy)lysine (poly(CBZ)lysine, 0.5 g, Sigma), and triethylamine (150 μl) in 25 ml DMFA. Poly(CBZ)lysine is poly-L-lysine protected at the epsilon position. The reaction was allowed to proceed until there was a negative ninhydrin reaction (e.g., overnight). The reaction mixture was then diluted with 150 ml $H_2O$ and subjected to ultrafiltration dialysis on an Amicon YM-100 membrane until there was a negative iodoform reaction on the filtrate. The mixture was concentrated to 25 ml on the same membrane and freeze-dried.

The resultant MPEG-succinate-poly (CBZ) lysine (0.89 g) was subjected to deprotection of the polymeric backbone's side groups with hydrogen bromide (HBr) in glacial acetic acid (10 ml) to form the block copolymer MPEG-poly-L-lysine (MPEG-PLL). The mixture was incubated for thirty minutes, and the resultant precipitate was washed three times with 30 ml of ethyl ether, and freeze-dried.

Addition of Radiopaque Molecules

The radiopaque molecule, triiodobenzoic acid, was covalently bound to MPEG-PLL as follows. Triiodobenzoic acid (4 g, Aldrich), dicyclohexylcarbodiimide (1.65 g, Sigma), and N-hydroxysuccinimide (0.92 g, Pierce) were dissolved in 30 ml dry DMFA and allowed to react overnight at room temperature with stirring. After filtration to remove isourea, the volume of DMFA was reduced under vacuum. The product, triiodobenzoic acid-N-hydroxysuccinimide (TIBA-NHS), was precipitated and washed in ice-cold isopropanol. The product was further recrystallized from the same solvent.

MPEG-PLL (0.82 g), triiodobenzoic acid N-hydroxysuccinimide ester (1 g) and triethylamine (90 μl) were incubated in 8 ml DMFA for two days. This procedure results in the maximal level of substitution on PLL by triiodobenzoic acid residues (80–90% substitution); higher levels of substitution cannot be achieved due to stearic hindrance. Unconjugated amino groups on PLL were blocked by adding acetic anhydride in 0.1 ml aliquots until a negative result was achieved upon ninhydrin reaction. Approximately 0.7 ml acetic anhydride was normally necessary per gram of MPEG-PLL.

Addition of Chelating Groups

To add chelating groups, e.g., in order to radioactively label the MICBCs, diethylenetriamine pentaacetic acid (DTPA) anhydride (50 mg) was added prior to the acetic anhydride. The volume was increased to 50 ml with $H_2O$, and the mixture was dialyzed against $H_2O$. The pH was adjusted to neutrality and the precipitated product, N,α-(ε-triiodobenzyl) PLL-MPEG, was isolated by centrifugation.

Optimizing Micelle Formation

For optimal micelle formation, the preferred sizes of the polymers are 10,000 to 15,000 d for the hydrophilic polymer, and 3000 to 6000 d for the polymeric backbone for the radiopaque residues. MICBCs comprising polymers of these sizes exist in vivo as micelles for forty minutes to two hours, at which time they dissociate into unimers.

When PEG of 20,000 d was used as a hydrophilic polymer, the synthesized agent was quickly taken up by the liver; therefore, this agent is not ideal for imaging of the blood pool. When MPEG-succinate of 5000 d was used as the hydrophilic polymer, and either ε-triiodobenzoyl polylysine (3000 to 5000 d) or triiodobenzoic acid N-hydroxysuccinimide was used as the hydrophobic polymer, the resulting compound did not form micelles. Micelles were formed when MPEG succinate or propionate of 12,000 d was linked to poly-L-lysine (PLL) of 3000 to 5000 d. Optimal results were obtained using a copolymer of MPEG, with a molecular weight of 12,000 d, and ε-triiodobenzoyl-PLL, in which the polymeric backbone, PLL, has a molecular weight of 3000, and the iodine-substituted PLL has a molecular weight of 9000 d. This molecule, designated TIBPL(9)-PEG(12), was therefore used in the following in vitro and in vivo studies.

In Vitro Studies

Figure 3:
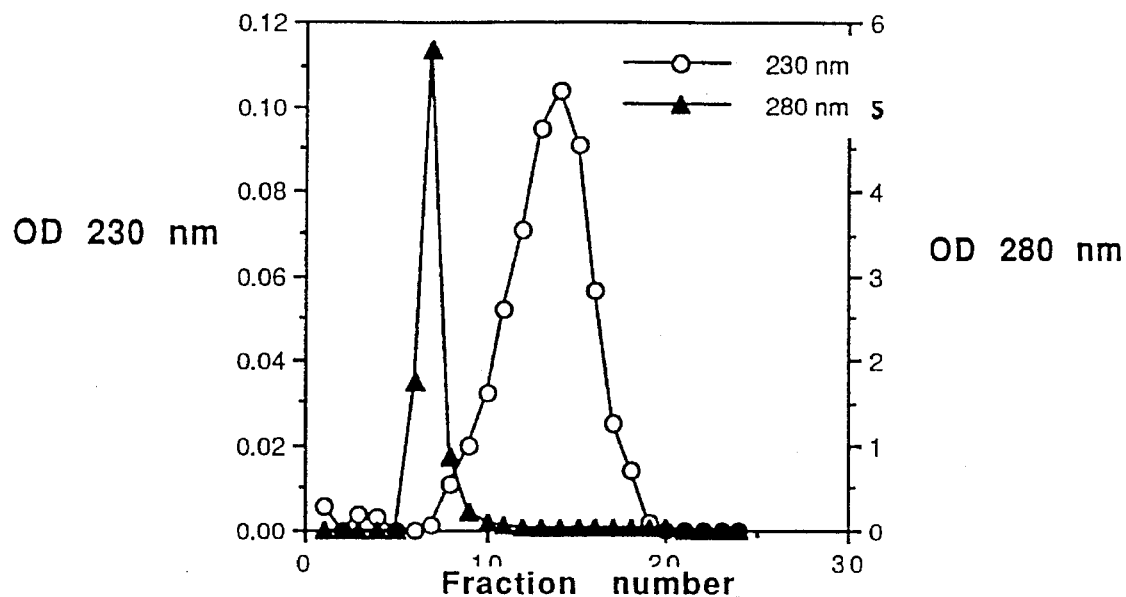
FIG. 3 is a gel permeation chromatograph of TIBPL-PEG having a TIBPL portion with a molecular weight of 9,000 daltons, and a PEG portion with a molecular weight of 12,000 daltons (TIBPL(9)-PEG(12)) and a methoxypolyethylene glycol (MPEG) polymer.
Figure 4:
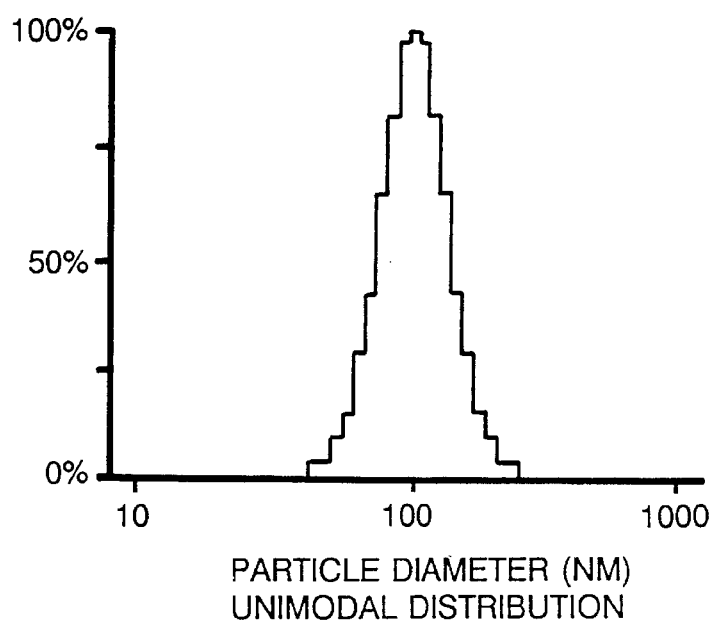
FIG. 4 is a graph illustrating the size distribution of TIBPL(9)-PEG(12).

Studies were carried out in vitro to characterize the structure of MICBCs. MICBCs and parent MPEG polymers in water or saline were subjected to conventional gel permeation chromatography through a 1×25 cm Bio-Gel A1.5 m column. As shown in the chromatograph of FIG. 3, TIBPL(9)-PEG(12) (▲) forms structures that can be distinguished from MPEG polymers (o) on the basis of size. The size distribution of the TIBPL(9)-PEG(12) is shown in the graph of FIG. 4. Laser light scattering of TIBPL(9)-PEG(12) was measured by a Coulter N4 submicron particle size analyzer. The results indicate that the diameter of TIBPL(9)-PEG(12) in aqueous solution is 100–150 nm.

Figure 5:
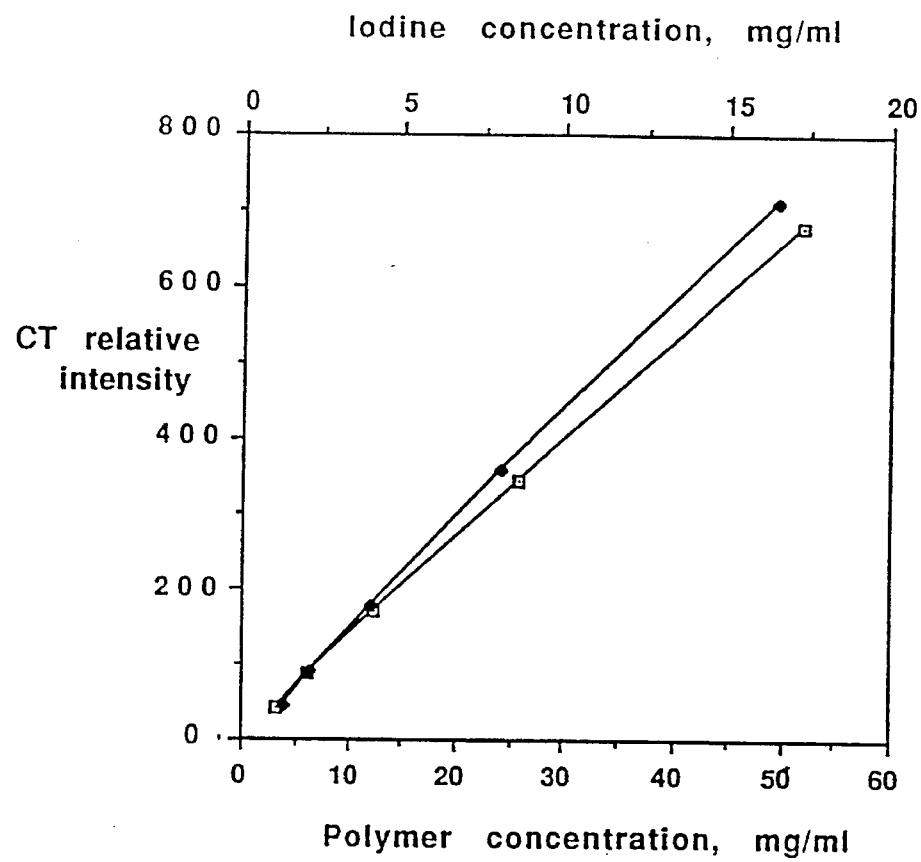
FIG. 5 is a graph illustrating the iodine content of TIBPL(9)-PEG(12) compared to standard contrast agents.

To determine the iodine content of the TIBPL(9)-PEG(12), aqueous preparations of TIBPL(9)-PEG(12) were serially diluted and subjected to CT scanning with a Toshiba TCT 900Sx/II CT scanner. The results were compared to the results obtained using standard preparations of OMNIPAQUE™ (iohexol), a commercially available iodine-containing radiographic contrast agent. FIG. 6 shows a representative CT scan of the serially diluted preparations. The results are also shown graphically in FIG. 5; the iodine content of the TIBPL(9)-PEG(12) (♦) is approximately 25% (w/w), and is roughly equivalent to the iodine content of the OMNIPAQUE™ (□) preparation used in this assay. The graph illustrates that the CT attenuation of similar concentrations of TIBPL(9)-PEG(12) and iohexol is similar.

In Vivo Studies

In vivo studies were conducted on mice and rabbits to determine the biodistribution and kinetics of blood clearance of MICBCs after intravenous administration. For these experiments, TIBPL(9)-PEG(12) labelled with $^{111}$In were used. Imaging with radiolabelled compounds permits the detection of much smaller quantities of compound than can be detected with CT, and is therefore more accurate in determining the biodistribution and pharmacokinetic properties of the compounds.

The labelling procedure was performed as follows. MPEG-PLL was synthesized and incubated with triiodobenzoic acid in DMFA as described above. The unconjugated ε-amino groups of PLL were then modified by addition of DTPA anhydride (50 mg). The DTPA anhydride/polymer reaction mixture was reconstituted with $H_2O$ and dialyzed. Labelling with $^{111}$In was carried out by transchelation in 0.1M citrate, pH 5.3. $^{111}$In in 0.1N HCl was added to 0.1 ml citrate buffer, incubated for fifteen minutes at room temperature, and added to 0.1–0.2 ml (50 to 100 μg) of the DTPA-modified MICBCs in $H_2O$. The mixture was incubated for one hour at room temperature with occasional vortexing. $^{111}$In-labelled MICBCs were purified from unincorporated $^{111}$In by gel filtration over a 1×30 cm Sephadex G-100 column.

$^{111}$In-labelled DTPA-modified TIBPL(9)-PEG(12) (50,000 to 200,000 cpm) were mixed with unlabelled TIBPL(9)-PEG(12), and 200 mg I per kilogram of body weight was injected via the tail vein into Balb/c mice (18–22 g) which had been anesthetized with ether. Rabbits were injected intravenously with 40–65 μCi $^{111}$In-labelled TIBPL(9)-PEG(12), or 20–35 μg per animal. The animals were sacrificed at time intervals, and samples were removed from blood and organs. The samples were then subjected to gamma counting to determine the amount of radioactivity they contained.

Figure 7:
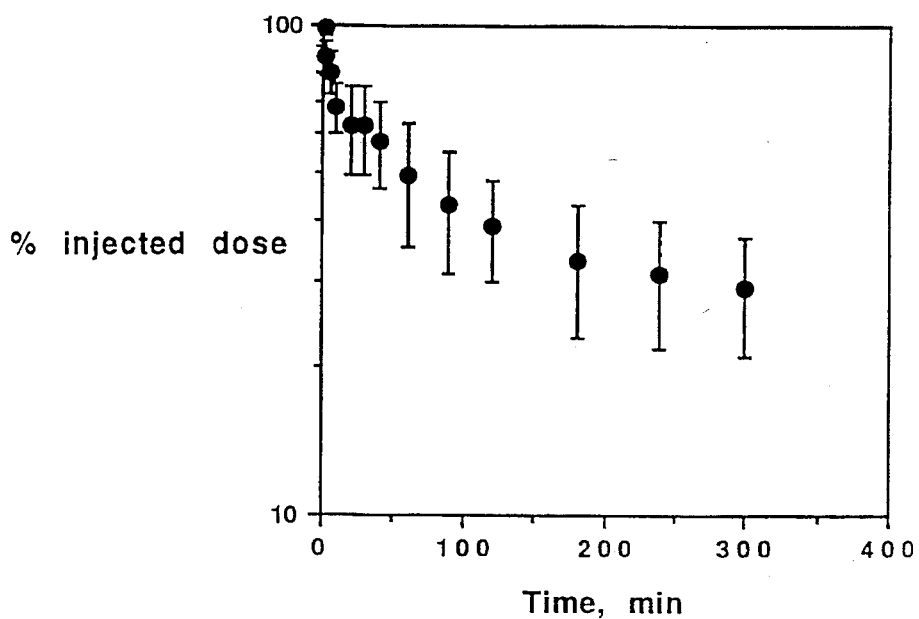
FIG. 7 is a graph showing the amount of $^{111}$In present in the blood of rabbits at various times subsequent to intravenous injection with $^{111}$In-labelled TIBPL(9)-PEG(12).

FIG. 7 shows the kinetics of blood clearance of $^{111}$In-labelled DTPA-TIBPL(9)-PEG(12) in rabbits. Fifty percent of the injected dose is detectable in the blood samples obtained one hour after administration, indicating that the half-life of TIBPL(9)-PEG(12) in the blood of rabbits is approximately one hour.

Figure 8:
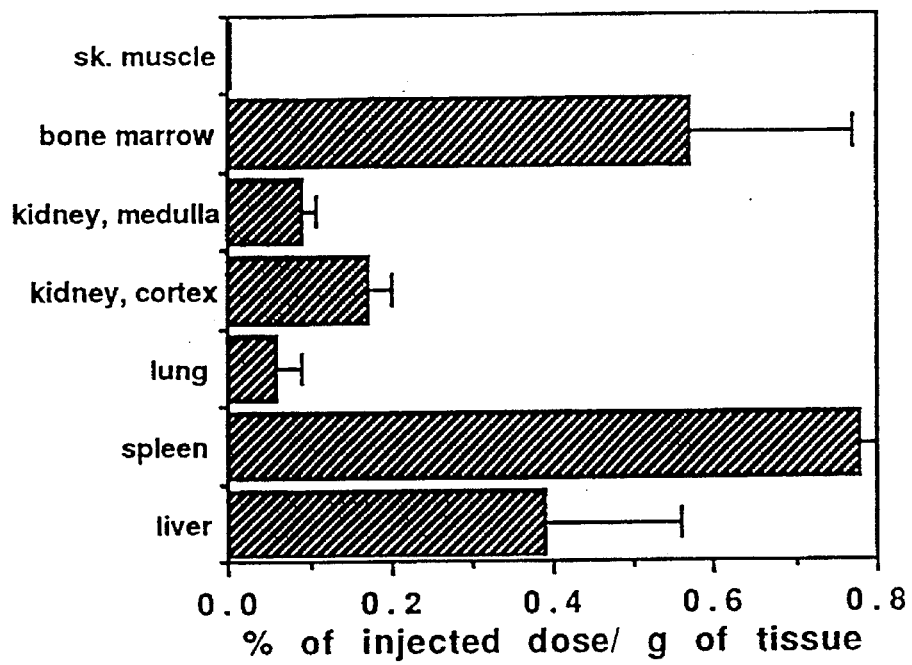
FIG. 8 is a bar graph showing the biodistribution of $^{111}$In in rabbits five hours after intravenous injection with $^{111}$In-labelled TIBPL(9)-PEG(12).
Figure 10:
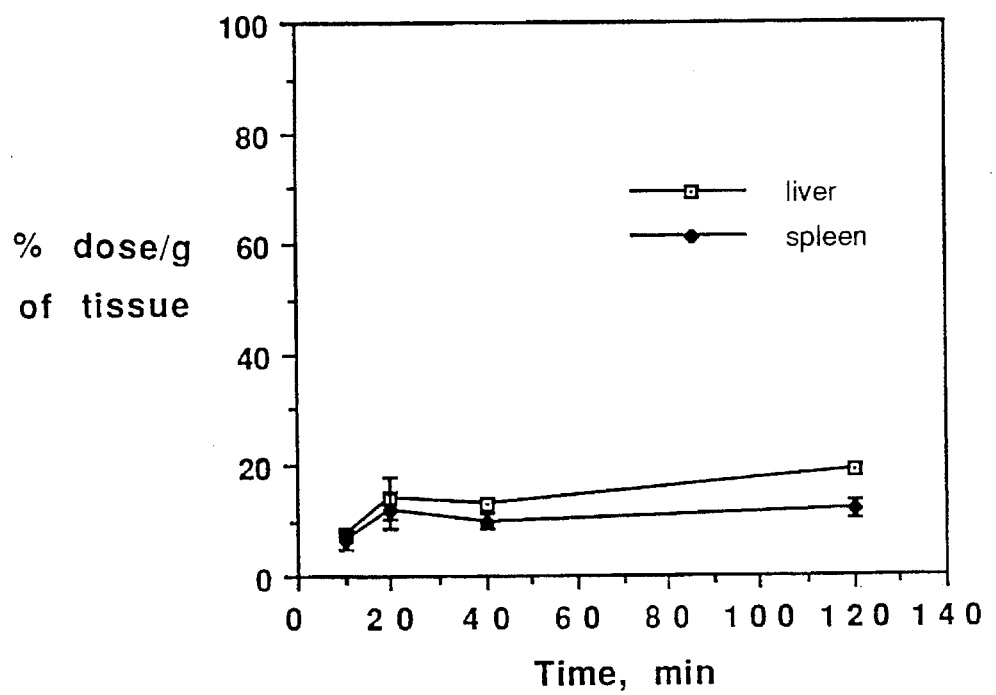
FIG. 10 is a graph showing the amount of $^{111}$In in the livers and spleens of mice at various times subsequent to intravenous injection of $^{111}$In-labelled TIBPL(9)-PEG(12).

Biodistribution studies were also performed on rabbits and mice injected with the $^{111}$In-labelled TIBPL(9)-PEG(12). $^{111}$In levels were determined at five hours post-injection. As shown in the bar graph of FIG. 8, the major areas of detection of $^{111}$In in the rabbit are the spleen, bone marrow, and liver. Accumulation of $^{111}$In mouse liver and spleen at various times subsequent to injection with $^{111}$In-labelled TIBPL(9)-PEG(12) is shown in the graph of FIG. 10. These experiments revealed limited accumulation of TIBPL(9)-PEG(12) in the liver (□) and spleen (♦), indicating that these MICBCs possess the ability to avoid the RES.

Additionally, as shown in FIGS. 9A to 9D, whole body radioscintigraphy reveals that a significant amount of $^{111}$In is located in the bladder subsequent to injection in the rabbit. In this experiment, rabbits were injected with 55 μCi $^{111}$In-labelled TIBPL(9)-PEG(12). Scintigraphy scans were obtained with a gamma camera at time intervals of 3, 10, 30, and 120 minutes after administration of these MICBCs (FIGS. 9A to 9D, respectively). The results indicate that TIBPL(9)-PEG(12) are eliminated from the body via the kidney.

Figure 11:
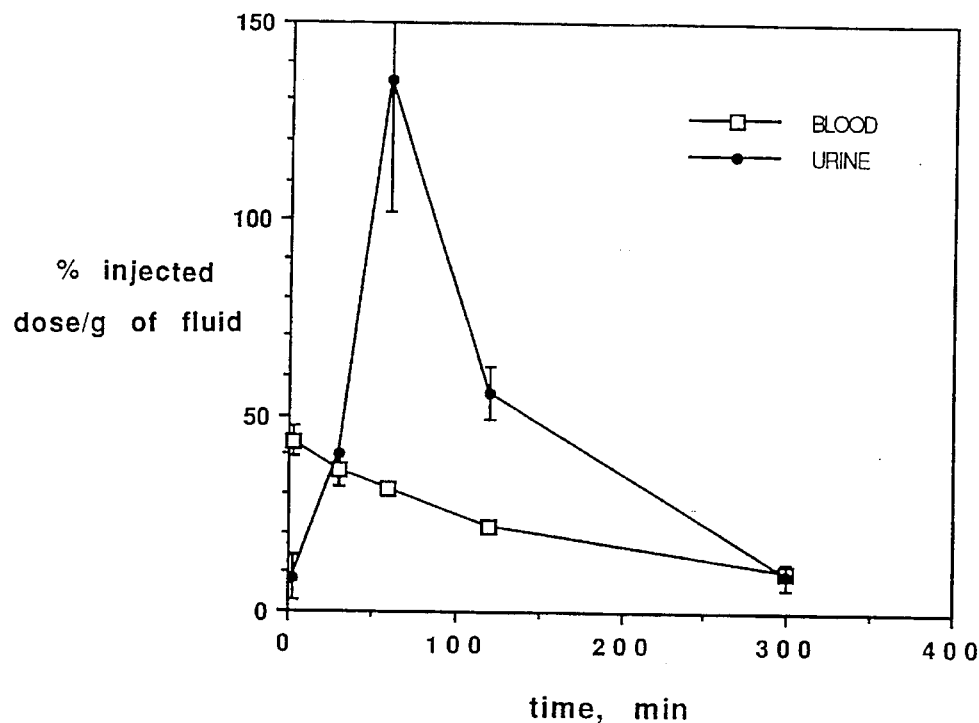
FIG. 11 is a graph showing the amount of $^{111}$In in the blood and urine of mice at various times subsequent to intravenous injection of $^{111}$In-labelled TIBPL(9)-PEG(12).

Experiments in mice showed that MICBCs can be efficiently cleared from the body. In these experiments, the amount of $^{111}$In in urine and blood of mice injected intravenously with $^{111}$In-labelled TIBPL(9)-PEG(12) (200 mg I/kg) was determined at various times post-injection. As shown in FIG. 11, the amount of $^{111}$In detected in urine (●) exceeded that detected in blood (□) one hour after injection of $^{111}$In-labelled TIBPL(9)-PEG(12), indicating that a substantial amount of the labelled material had been excreted via the kidney.

Figure 12:
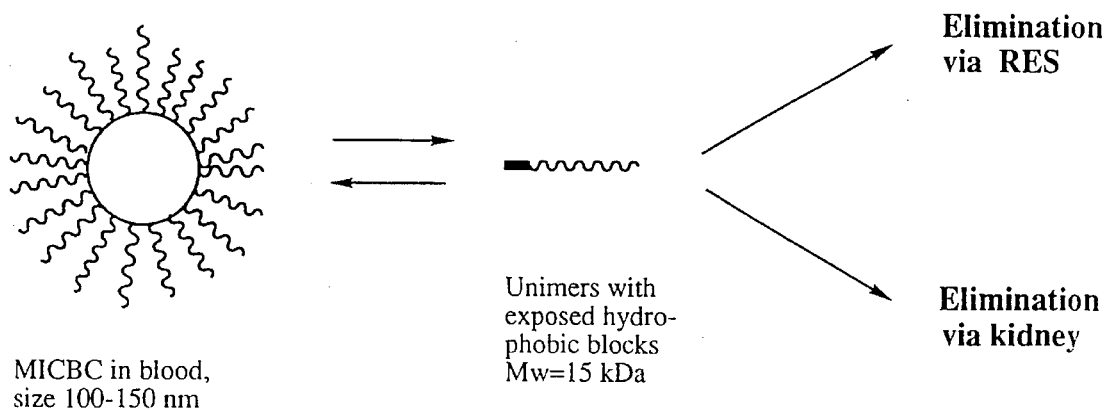
FIG. 12 is a schematic diagram showing dissociation of MICBCs and natural mechanisms for removal of dissociated unimers.

The proposed in vivo degradation pathway of MICBCs upon intravenous administration is illustrated in FIG. 12. Upon injection, MICBCs exist in the blood as micelles of approximately 100–150 nm, which are initially protected from degradation. MICBCs circulate in the blood, and there is a limited accumulation of MICBCs in organs of the RES, i.e., liver and spleen. As MICBCs are diluted in the circulation, however, they begin to dissociate into unimers composed of individual polymer chains. Some of these unimers become associated with plasma constituents, and are subsequently taken up by the RES. However, the small size of the unimers (approximately 15,000 d for the unsubstituted block copolymer, MPEG-PLL) allows them to be excreted via the kidney, and many are therefore eliminated from the body.

The particulate nature of the MICBCs was demonstrated in lymphoscintigraphy experiments. In these experiments, TIBPL(9)-PEG(12) labelled with $^{111}$In (approximately 50 μCi) were injected subcutaneously into the forepaws of rabbits, and lymphoscintigraphy was performed on the injected animals. FIG. 13 is a representative lymphoscintigraphy scan, which shows the high levels of TIBPL(9)-PEG(12) detected in the lymph nodes of injected rabbits. There was no change in the intensity of the images of the lymph nodes at 3, 6, 30, and 120 minutes post injection, indicating that accumulation in the lymph nodes occurs rapidly and that MICBC are maintained in the lymph nodes. TIBPL(9)-PEG(12) can be detected in the subscapular lymph nodes of injected animals within seconds of administration of the labelled material.

The table below shows the in vivo distribution in a rabbit at two hours post-injection of $^{111}$In-labelled MICBC injected subcutaneously into the rabbit's paw. Significant amounts of the injected $^{111}$In-labelled MICBC preparation were detected in the axillary and subscapular lymph node (LN; 50.4 and 74.1% of injected dose per gram of tissue, respectively), while little was detected in blood, liver, kidney or bone marrow.

TABLE

| ORGAN | Accumulation (% injected dose per gram of tissue) | Standard Error of mean |
| --- | --- | --- |
| Axillary LN | 50.40 | 13.20 |
| Subscapular | 74.10 | 19.60 |
| Blood | 0.05 | 0.02 |
| Liver | 0.03 | 0.01 |
| Kidney medulla– | 0.03 | 0.02 |
| Kidney cortex | 0.05 | 0.04 |
| Bone marrow | 0.03 | 0.02 |

Diagnostic Use of MICBC

Figure 14A:
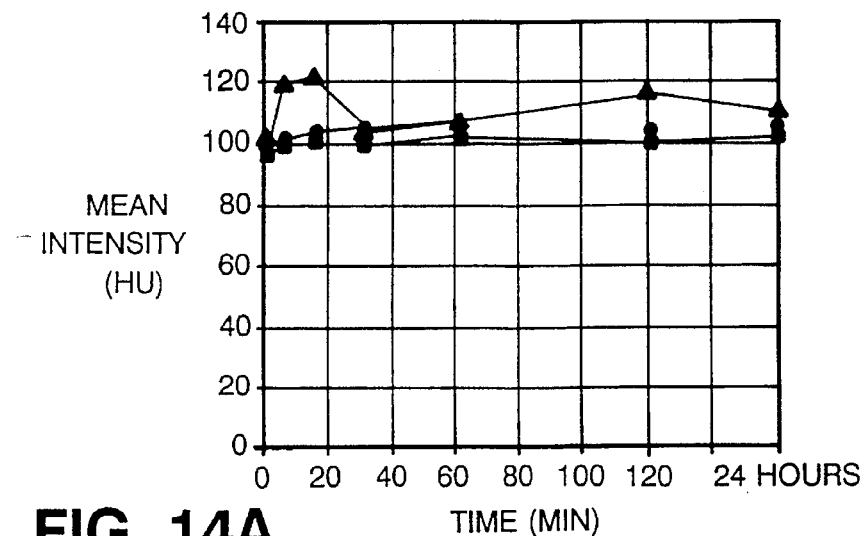
FIGS. 14A to 14C are graphs showing the CT intensity of liver, blood, and spleen, respectively, of rats at various times subsequent to injection with various concentrations of TIBPL(9)-PEG(12).
Figure 14B:
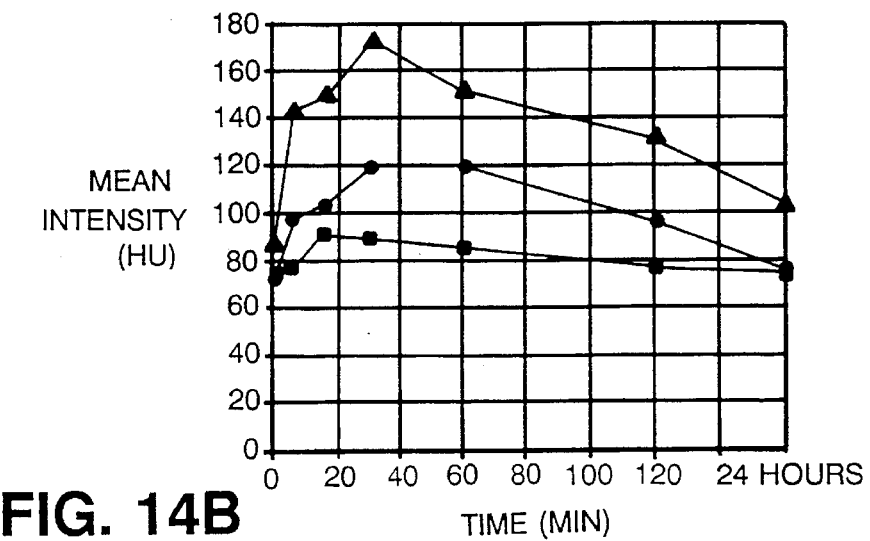
Figure 14C:
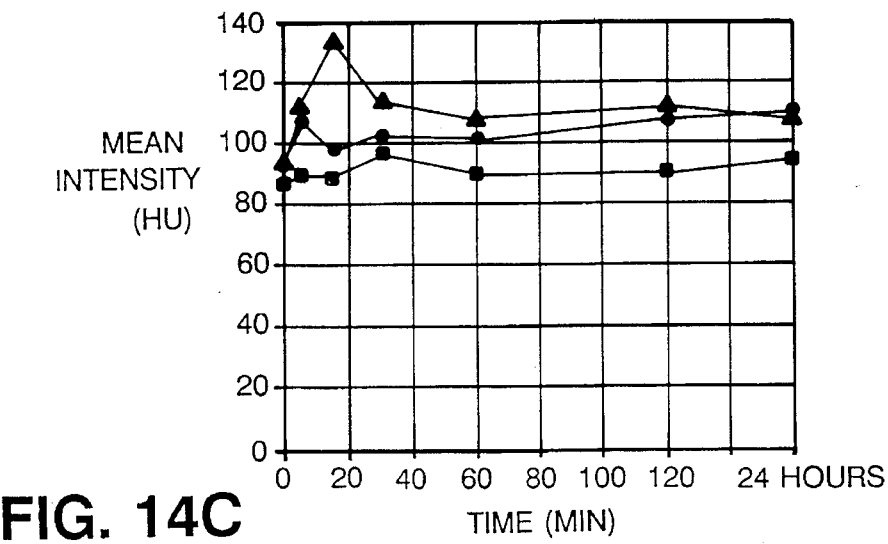

CT scanning was performed on rats and rabbits injected with MICBCs in order to determine the efficacy of MICBCs as a CT contrast agent. The animals were anesthetized with Ketamine (40 mg/kg of body weight) and Xylazine (5 mg/kg of body weight). TIBPL(9)-PEG(12) (in HEPES-buffered saline, pH 7.4; 50–250 mg I per kg body weight) were injected intravenously via the tail vein (in rats) or the ear vein (in rabbits). CT scanning was performed using a Toshiba TCT 900Sx/II scanner at time intervals of 5, 15, 30, 60 and 120 minutes, and at 24 hours post-injection. CT attenuation was measured in the liver, blood, and spleen. The data acquired were analyzed using "DIP Station" software for the Apple Macintosh. The results are shown in FIGS. 14A to 14C (A, liver; B, blood; C, spleen).

As shown in these graphs, subsequent to the intravenous administration of MICBCs, the liver and spleen showed peak attenuation on CT scanning at approximately fifteen minutes. The blood pool (FIG. 14B) showed significant attenuation for one to two hours following MICBC administration. The enhancement profiles of liver (FIG. 14A), spleen (FIG. 14C), and blood (FIG. 14B) displayed a dose dependence on TIBPL(9)-PEG(12), with a dose of 100 mg I per kg (▲) producing a more intense signal than 50 (●) or 25 (■) mg I per kg. These findings indicate that MICBC are effective CT imaging agents for the liver, spleen, and blood pool.

For use in humans, the contrast agent can be administered intravenously or subcutaneously, depending on the organ or tissue to be imaged. Subcutaneous administration allows imaging of lymph nodes, while intravenous administration allows imaging of any vascularized regions of the body. Optimal dosage for intravenous administration is approximately 200 to 250 mg I/kg of body weight. CT imaging can be performed using CT scanners by methods known to those skilled in the art.

MICBCs as Targeted Diagnostic Agents

The micelles of the invention can also be targeted to specific regions of the body by attachment of specific targeting ligands to provide rapid accumulation and concentration of micelles and, correspondingly, of radiopaque molecules, in a designated tissue or tumor, for example. This method permits visualization of the target area for substantially longer than one hour, even at the same rate of micelle dissociation into unimers, since a much higher initial level of radiopaque molecules is achieved.

Targeting ligands are any ligand specific for a characteristic component of the targeted region. Preferred targeting ligands include proteins such as polyclonal or monoclonal antibodies, antibody fragments, or chimeric antibodies, enzymes, or hormones, or sugars such as mono-, oligo- and poly-saccharides. Suitable antibodies include any that are specific for endothelial cells of the target organ, or for structures of the target organ exposed to the circulation as a result of local pathology, such as myocardial infarction, tumor, thrombus, or atheroma. For example, antibodies to fibrin, thrombospondin, endothelial cells, proliferating smooth muscle cells, or tumor antigens can be used to target the MICBCs.

The targeting ligand can be either anchored in the hydrophobic core of the micelle or attached to the reactive terminal groups of the hydrophilic portion of the micelle. For anchoring a targeting ligand into the hydrophobic core, the targeting ligand must be preliminarily modified with a hydrophobic compound, such as long-chain fatty acid acyl, phospholipid, etc. The targeting ligand can be modified with the hydrophobic compound by standard modification techniques for hydrophilic compounds with hydrophobic groups.

Alternatively, the targeting ligand can be attached to the micelle via a linkage to a reactive group, e.g., on the distal end of the hydrophilic polymer. Preferred reactive groups include amino groups, carboxylic groups, hydrazide groups, and thiol groups. The coupling of the targeting ligand to the hydrophilic polymer can be performed by standard methods of organic chemistry which are known to those skilled in the art.

The total concentration of the targeting ligand in the MICBC can be from 0.01 to 10% mol, preferably, from 0.1 to 1.0% mol.

Other Embodiments

It is to be understood that while the invention has been described in conjunction with the detailed description above, the foregoing description is intended to illustrate and not limit the scope of the invention, which is defined by the scope of the claims. Other aspects, advantages, and modifications within the scope of the invention will be apparent to those skilled in the art to which the invention pertains.

What is claimed is:

1. A compound capable of reversibly forming micelles in an aqueous solution, said compound comprising a hydrophilic polymer linked to a hydrophobic polymer, and said hydrophobic polymer comprising a backbone incorporating radiopaque molecules via covalent bonds, wherein said micelles dissociate in vivo into said compound over a 24 hour period.

2. A compound of claim 1, wherein said hydrophilic polymer is polyethylene oxide, polyvinylpyrrolidone, polyacrylamide, poly-(N-hydroxypropyl)-methacrylamide, polyvinylalcohol, a polymethacrylate, a polysaccharide, a polyamino acid, or a polyacrylic ester, or a derivative thereof.

3. A compound of claim 1, wherein said hydrophilic polymer is polyethylene glycol.

4. A compound of claim 1, wherein said backbone is an amino-containing polymer, a polymer of amino acids, a polycarboxylic acid, a polyanhydride, a polyhydroxy acid, a polysaccharide, polystyrene, polyisoprene, polyalkalene oxide, or a derivative thereof.

5. A compound of claim 4, wherein said backbone is poly-L-lysine.

6. A compound of claim 1, wherein said radiopaque molecule comprises an element with a heavy nucleus.

7. A compound of claim 6, wherein said radiopaque molecule comprises iodine.

8. A compound of claim 7, wherein said radiopaque molecule is diatrizoate, iothalamate, metrizoate, or iodipamide.

9. A compound of claim 1, wherein said radiopaque molecule is triiodobenzoic acid.

10. A compound of claim 1, wherein said radiopaque molecule comprises bromine.

11. A compound of claim 10, wherein said radiopaque molecule is perfluorooctyl bromide (PFOB).

12. A compound of claim 1, wherein said hydrophilic polymer has a molecular weight of 10,000 to 15,000 daltons, and said backbone has a molecular weight of 3000 to 6000 daltons.

13. A compound of claim 1, wherein said hydrophilic polymer is polyethylene glycol, and said backbone is poly-L-lysine.

14. A compound of claim 13, wherein said polyethylene glycol has a molecular weight of 12,000 daltons, and said hydrophobic polymer has a molecular weight of 9,000.

15. A compound of claim 14, wherein said radiopaque molecule is triiodobenzoic acid.

16. A method of imaging a region in a patient, said method comprising administering a diagnostically effective amount of a compound of claim 1 in the form of micelles to the patient, exposing said region to radiation, and obtaining an image of said region by detecting said micelles of said compound.

17. A method of claim 16, wherein said region is the blood pool.

18. A method of claim 16, wherein said region is the liver or spleen.

19. A method of claim 16, wherein said region is the lymph nodes.

20. A radiographic imaging agent comprising a plurality of block copolymers forming a micelle, said block copolymers comprising a hydrophilic polymer linked to a hydrophobic polymer, and said hydrophobic polymer comprising a backbone incorporating radiopaque molecules via covalent bonds.

* * * * *

UNITED STATES PATENT AND TRADEMARK OFFICE
CERTIFICATE OF CORRECTION

PATENT NO.   : 5,567,410

DATED        : October 22, 1996

INVENTOR(S)  : Vladimir P. Torchilin et al.

It is certified that error appears in the above-identified patent and that said Letters Patent is hereby corrected as shown below:

<u>In the Title</u>: Item [54] and Column 1, line 1,

Delete "Composotions" and insert therefor
-- Compositions --;

Col. 3, line 22, delete "triiodobenzyl" and insert therefor -- triiodobenzoyl --;

Col. 8, line 4, delete "$^{111}$In mouse" and insert therefor --$^{111}$In in mouse";

Col. 9, line 26, delete "Macintosh" and insert therefor -- MacIntosh --.

Signed and Sealed this

Eighth Day of December, 1998

*Attest:*

*Attesting Officer*

BRUCE LEHMAN

*Commissioner of Patents and Trademarks*